US010945738B2

(12) United States Patent
Auld et al.

(10) Patent No.: US 10,945,738 B2
(45) Date of Patent: Mar. 16, 2021

(54) TUNABLE MAGNETIC SPHINCTER AUGMENTATION DEVICE

(71) Applicants: Torax Medical, Inc., Shoreview, MN (US); Ethicon LLC, Guaynabo, PR (US)

(72) Inventors: Michael D. Auld, Blue Ash, OH (US); Lauren E. Flakne, Cincinnati, OH (US); Kyle P. Taylor, Greenfield, MN (US); Jerome K. Grudem, Jr., Rogers, MN (US); Celeste L. Huster, Blaine, MN (US)

(73) Assignees: Torax Medical, Inc., Shoreview, MN (US); Ethicon LLC, Guaynabo, PR (US)

( * ) Notice: Subject to any disclaimer, the term of this patent is extended or adjusted under 35 U.S.C. 154(b) by 334 days.

(21) Appl. No.: 15/914,381

(22) Filed: Mar. 7, 2018

(65) Prior Publication Data

US 2019/0274689 A1  Sep. 12, 2019

(51) Int. Cl.
*A61B 17/12* (2006.01)
*A61F 5/00* (2006.01)
(Continued)

(52) U.S. Cl.
CPC .. *A61B 17/12013* (2013.01); *A61B 17/12009* (2013.01); *A61F 5/0079* (2013.01);
(Continued)

(58) Field of Classification Search
CPC ........ A61B 17/12009; A61B 17/12013; A61B 2017/00827; A61B 2017/00477;
(Continued)

(56) References Cited

U.S. PATENT DOCUMENTS 6,543,456 B1   4/2003   Freeman
7,175,589 B2   2/2007   Deem et al.
(Continued)

FOREIGN PATENT DOCUMENTS

WO   WO 2018/001192 A1   1/2018

OTHER PUBLICATIONS

International Search Report and Written Opinion dated May 27, 2019 for Application No. PCT/IB2019/051864, 13 pgs.
(Continued)

*Primary Examiner* — Thaddeus B Cox
(74) *Attorney, Agent, or Firm* — Frost Brown Todd LLC

(57) ABSTRACT

An apparatus includes a plurality of beads, a plurality of links, a clasp assembly, and an adjustment feature. Each bead includes a housing, a passageway extending through the housing, and at least one annular magnet. The at least one annular magnet is coaxially positioned about the passageway. The links join the beads together. Portions of the links are slidably disposed in corresponding passageways of the beads. The clasp assembly is configured to removably secure the beads and links in a loop formation. The adjustment feature is operable to adjust an effective circumference of the loop formation. The adjustment feature may be incorporated into one or both of the clasp assembly or at least one of the beads.

20 Claims, 18 Drawing Sheets

(51) Int. Cl.
*A61B 17/00* (2006.01)
*A61F 2/04* (2013.01)
*A61B 5/055* (2006.01)

(52) U.S. Cl.
CPC ..... *A61B 5/055* (2013.01); *A61B 2017/00477* (2013.01); *A61B 2017/00827* (2013.01); *A61B 2017/00876* (2013.01); *A61F 2002/044* (2013.01)

(58) Field of Classification Search
CPC ......... A61B 2017/00876; A61F 5/0079; A61F 2002/044
See application file for complete search history.

(56) References Cited

U.S. PATENT DOCUMENTS

| | | | |
|---|---|---|---|
| 7,445,010 B2 | 11/2008 | Kugler et al. | |
| 7,695,427 B2 | 4/2010 | Kugler et al. | |
| 8,070,670 B2 | 12/2011 | Deem et al. | |
| 8,603,023 B2 | 12/2013 | Albrecht et al. | |
| 8,617,049 B2 | 12/2013 | Dlugos, Jr. et al. | |
| 8,636,751 B2 | 1/2014 | Albrecht et al. | |
| 8,734,475 B2 | 5/2014 | Ekvall et al. | |
| 8,870,742 B2 | 10/2014 | Dlugos, Jr. et al. | |
| 8,876,761 B2 | 11/2014 | Albrecht et al. | |
| 2005/0002984 A1 | 1/2005 | Byrum et al. | |
| 2005/0283235 A1* | 12/2005 | Kugler | A61F 5/0069 623/14.13 |
| 2007/0265646 A1 | 11/2007 | McCoy et al. | |
| 2011/0098731 A1 | 4/2011 | Whitbrook et al. | |

OTHER PUBLICATIONS

U.S. Appl. No. 15/664,665 entitled "Method for Assisting a Sphincter," filed Jul. 31, 2017.

* cited by examiner

TUNABLE MAGNETIC SPHINCTER AUGMENTATION DEVICE

FIELD OF THE INVENTION

The invention pertains to a sphincter augmentation device. More specifically, the invention pertains to a sphincter augmentation device that may be adjusted to vary a restrictive force imposed by the device on an anatomical structure.

BACKGROUND

In some instances, it may be desirable to place a medical implant within or surrounding a biological lumen/passageway in order to improve or assist the function of, or otherwise affect, the biological lumen/passageway. Examples of such biological lumens/passageways include, but are not limited to, the esophagus, a fallopian tube, a urethra, or a blood vessel. Some biological passages normally function by expanding and contracting actively or passively to regulate the flow of solids, liquids, gasses, or a combination thereof. The ability of a biological passage to expand and contract may be compromised by defects or disease. One merely illustrative example of a condition associated with decreased functionality of a body passage is Gastro Esophageal Reflux Disease ("GERD"), which effects the esophagus.

A normal, healthy, esophagus is a muscular tube that carries food from the mouth, through the chest cavity and into the upper part of the stomach. A small-valved opening in the esophagus, called the lower esophageal sphincter ("LES"), regulates the passage of food from the esophagus into the stomach, as well as the passage of acidic fluids and food from the stomach toward the esophagus. The LES may also regulate stomach intra-gastric pressures. A healthy LES may contain pressure of gasses within the stomach at around 10 mm Hg greater than normal intragastrical pressure, thereby impeding acidic gases/fluids from refluxing from the stomach back into the esophagus. When functioning properly, a pressure difference greater than 10 mm Hg may regulate when the LES opens to allow gasses to be vented from the stomach toward the esophagus.

If the LES relaxes, atrophies, or degrades for any reason, the LES may cease functioning properly. Therefore, the LES may fail to sufficiently contain pressure of gasses within the stomach such that acidic contents of the stomach may travel back into the esophagus, resulting in reflux symptoms. Two primary components that control the LES are the intrinsic smooth muscle of the distal esophagus wall and the skeletal muscle of the crural diaphragm or esophageal hiatus. A causation of esophageal reflux, which may be associated with GERD, is relaxation of one or both of the smooth muscle of the distal esophagus wall or the hiatal diaphragm sphincter mechanisms. Chronic or excessive acid reflux exposure may cause esophageal damage. Conventionally, treatment for GERD may involve either open or endoscopic surgical procedures. Some procedures may include a fundoplication that mobilizes of the stomach relative to the lower esophagus, or suturing a pleat of tissue between the LES and the stomach to make the lower esophagus tighter.

Examples of devices and methods that have been developed to treat anatomical lumens by providing sphincter augmentation are described in U.S. Pat. No. 7,175,589, entitled "Methods and Devices for Luminal and Sphincter Augmentation," issued Feb. 13, 2007, the disclosure of which is incorporated by reference herein; U.S. Pat. No. 7,695,427, entitled "Methods and Apparatus for Treating Body Tissue Sphincters and the Like," issued Apr. 13, 2010, the disclosure of which is incorporated by reference herein; U.S. Pat. No. 8,070,670, entitled "Methods and Devices for Luminal and Sphincter Augmentation," issued Dec. 6, 2011, the disclosure of which is incorporated by reference herein; and U.S. Pat. No. 8,734,475, entitled "Medical Implant with Floating Magnets," issued May 27, 2014, the disclosure of which is incorporated by reference herein.

While various kinds and types of instruments have been made and used to treat or otherwise engage anatomical lumens, it is believed that no one prior to the inventors has made or used an invention as described herein.

SUMMARY OF THE INVENTION

An apparatus includes a plurality of beads, a plurality of links, a clasp assembly, and an adjustment feature. Each bead includes a housing, a passageway extending through the housing, and at least one annular magnet. The at least one annular magnet is coaxially positioned about the passageway. The links join the beads together. Portions of the links are slidably disposed in corresponding passageways of the beads. The clasp assembly is configured to removably secure the beads and links in a loop formation. The adjustment feature is operable to adjust an effective circumference of the loop formation. The adjustment feature may be incorporated into one or both of the clasp assembly or at least one of the beads.

A method is used to adjust a restriction on an anatomical structure in a patient. The restriction is provided by an apparatus comprising a plurality of beads joined together by a plurality of links to form a loop. The beads comprise magnets magnetically urging the beads toward each other. The loop is installed around the anatomical structure. The method includes enlarging an effective circumference of the loop after the loop has been installed around the anatomical structure to form the restriction.

A method is used to adjust a restriction on an anatomical structure in a patient. The restriction is provided by an apparatus comprising a plurality of beads joined together by a plurality of links to form a loop. The beads comprise magnets magnetically urging the beads toward each other. The loop is installed around the anatomical structure. The magnets have a first magnetic strength upon installation of the loop around the anatomical structure. The method includes exposing the magnets to a magnetic field and thereby reducing the magnetic strength of the magnets to a second magnetic strength after the loop has been installed around the anatomical structure to form the restriction. The second magnetic strength is weaker than the first magnetic strength. The reduction of the magnetic strength of the magnets results in enlargement of an effective circumference of the loop.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
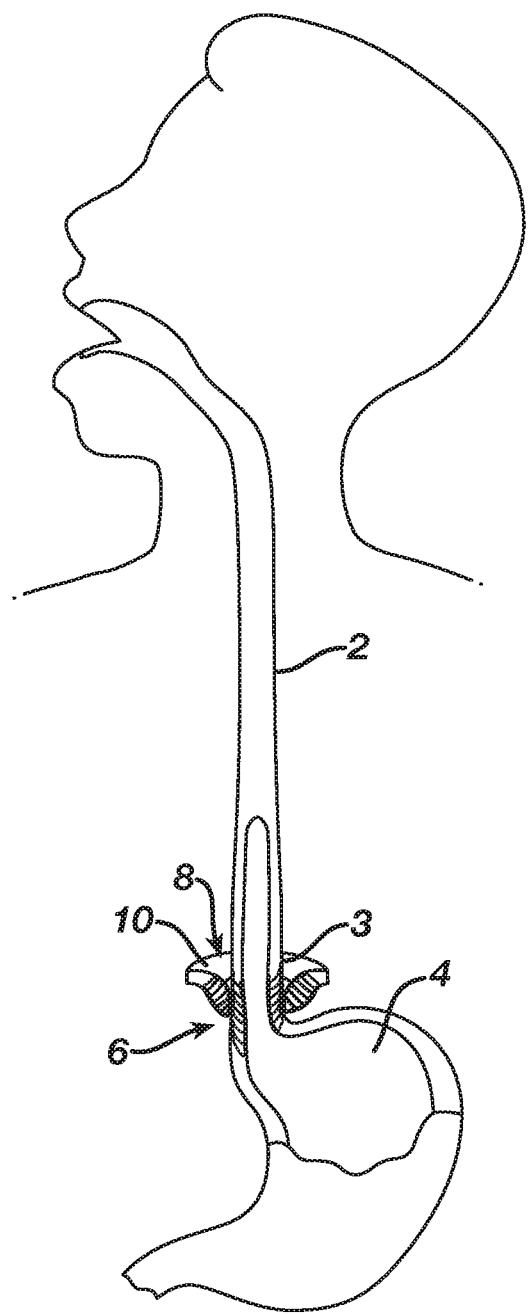
FIG. 1 depicts a cross-sectional side view, taken along a coronal plane of the body, of a biological passage.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. OVERVIEW OF EXEMPLARY SPHINCTER AUGMENTATION DEVICE

Figure 2:
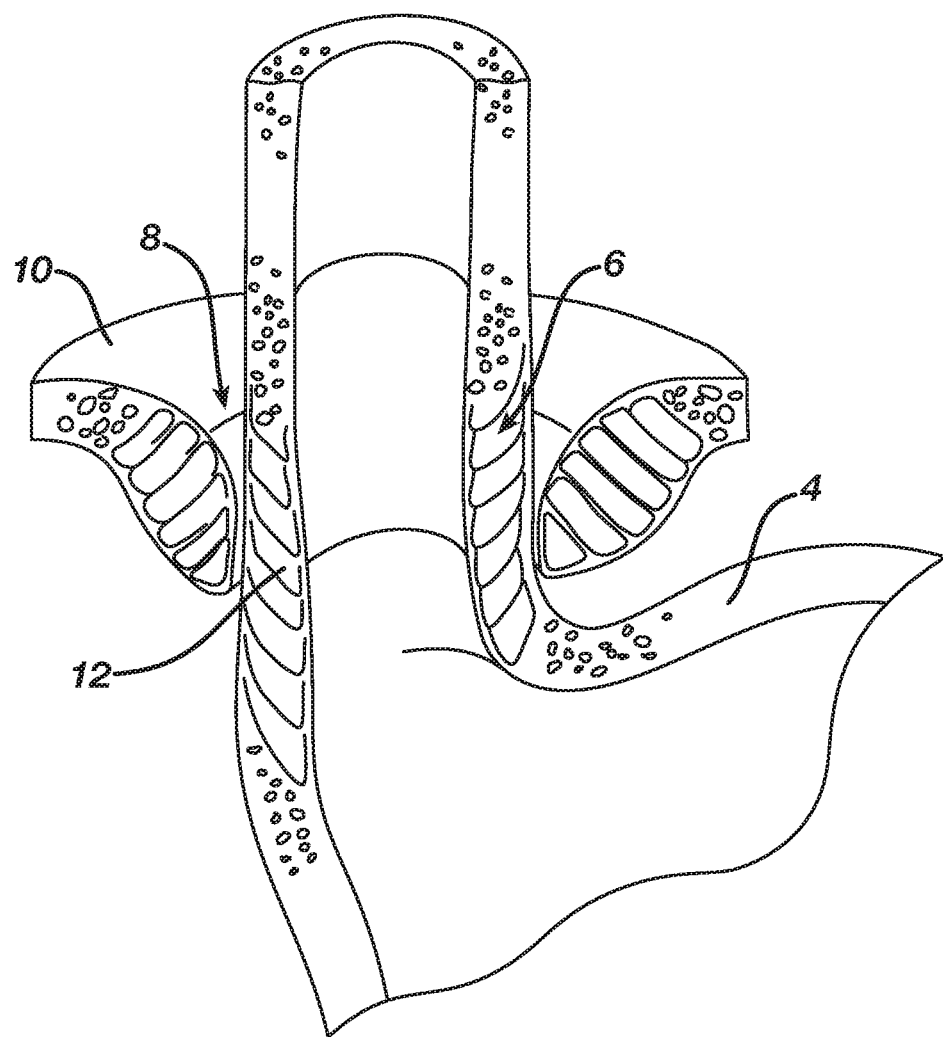
FIG. 2 depicts a cross-sectional isometric view, taken along a coronal plane of the body, of a human esophago-gastric junction.
Figure 3:
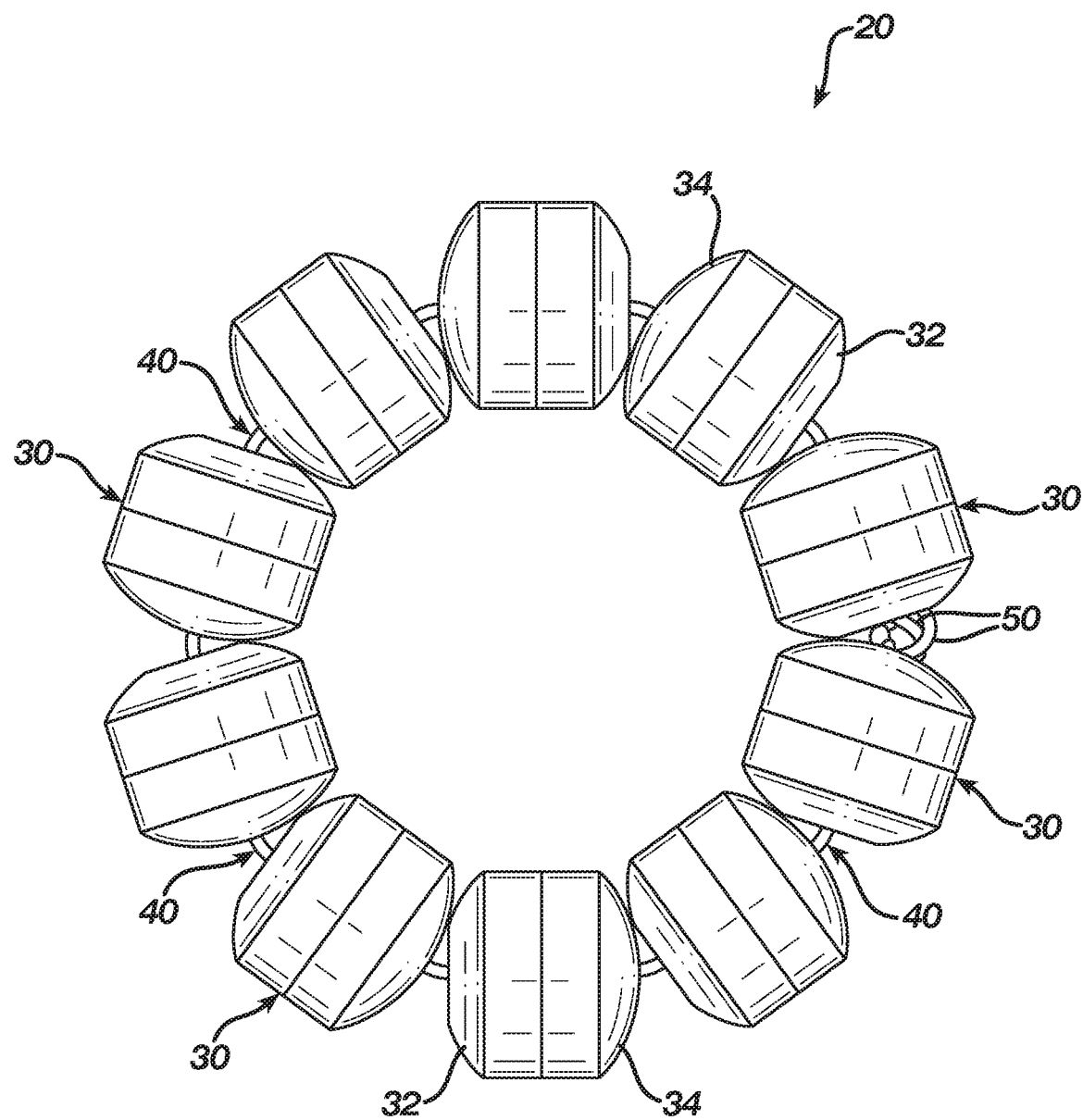
FIG. 3 depicts a top plan view of an exemplary sphincter augmentation device.

FIGS. 1-2 show selected portions of human anatomy, which includes an esophagus (2) extending from the mouth, through a hiatus (8) defined by a diaphragm (10), and into a stomach (4). Esophagus (2) also includes a distal esophagus (3) and an LES (6). LES (6) is located along distal esophagus (3) adjacent to the junction of esophagus (2) and stomach (4). The portion of LES (6) extending through hiatus (8) is supported by diaphragm (10). When functioning properly, LES (6) is configured to transition between an occluded state and an opened state (as shown in FIG. 2). As best seen in FIG. 2, LES (6) includes a plurality of sling fibers (12). Sling fibers (12) are smooth muscle tissue that may help regulate LES (6) transition between the occluded state and the open state. Hiatus (8) of diaphragm (10) may also help LES (6) transition between the occluded state and the open state.

A healthy LES (6) transitions between the occluded state and the opened state to act as a valve. In other words, a healthy LES (6) may transition from the occluded state to the opened state to allow solids, liquids, and/or gasses to selectively travel between esophagus (2) and stomach (4). For example, a healthy LES (6) may transition from the occluded state to the opened state to permit a bolus of food to travel from esophagus (2) into stomach (4) during peristalsis; or to vent intra-gastric pressure from stomach (4) toward esophagus (2). Additionally, in the occluded state, a healthy LES (6) may prevent digesting food and acidic fluid from exiting stomach (4) back into esophagus (2).

If LES (6) ceases functioning properly by prematurely relaxing, and thereby improperly transitioning esophagus (2) from the occluded state to the opened state, undesirable consequences may occur. Examples of such undesirable consequences may include acidic reflux from stomach (4) into esophagus (2), esophageal damage, inflamed or ulcerated mucosa, hiatal hernias, other GERD symptoms, or other undesirable consequences as will be apparent to one having ordinary skill in the art in view of the teachings herein. Therefore, if an individual has an LES (6) that prematurely relaxes, causing improper transitions from the occluded state to the opened state, it may be desirable to insert an implant around a malfunctioning LES (6) such that the implant and/or LES (6) may properly transition between the occluded state and the opened state.

Figure 4:
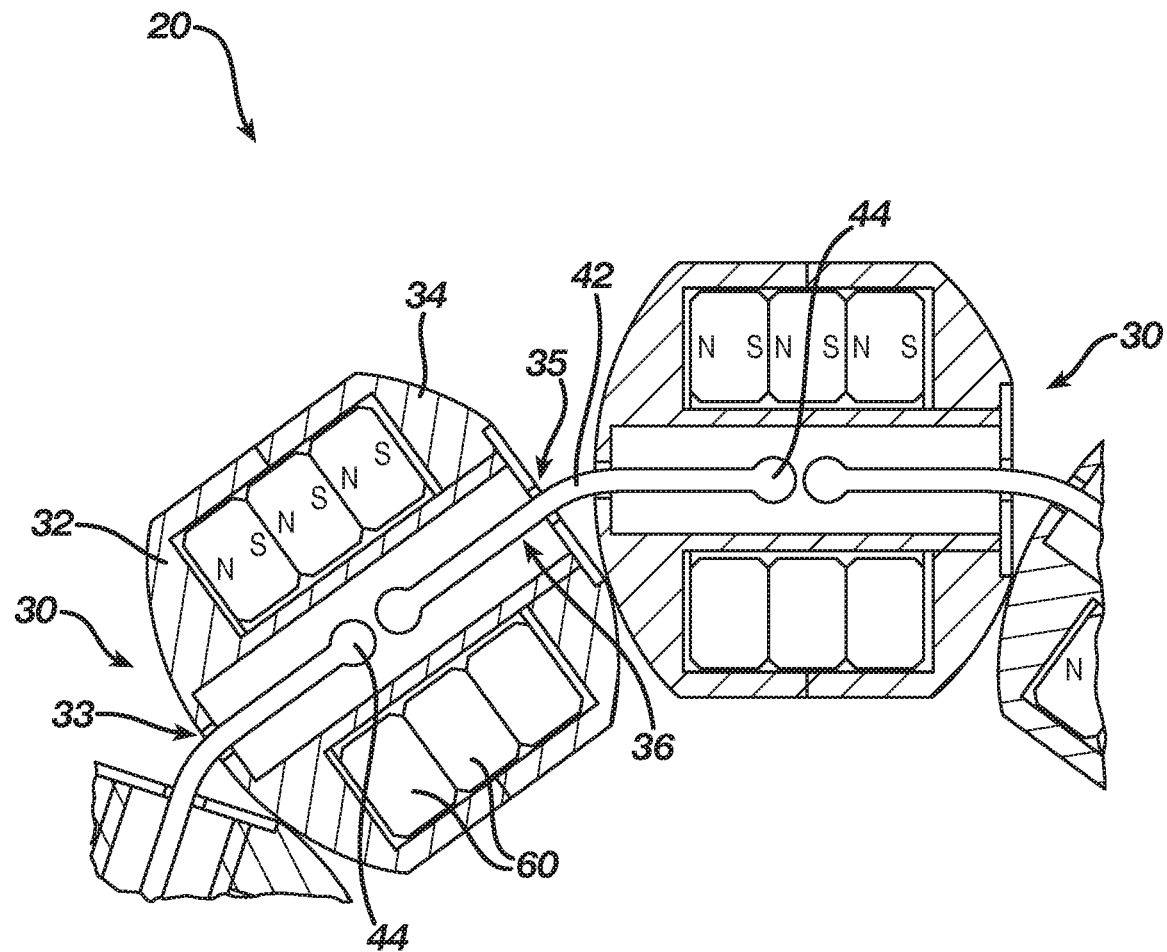
FIG. 4 depicts a partial, cross-sectional view of a portion of the sphincter augmentation device of FIG. 3.

FIGS. 3-5B show an exemplary sphincter augmentation device (20) that may be used as an implant around a malfunctioning LES (6) to assist the LES (6) in transitioning between the occluded state and the opened state. Device (20) of this example comprises a plurality of beads (30) that are joined together by a plurality of links (40). Each bead (30) comprises a pair of housings (32, 34) that are securely fastened to each other. By way of example only, housings (32, 34) may be formed of a non-ferrous material (e.g., titanium, plastic, etc.). Each bead (30) further comprises a plurality of annular or toroidal rare-earth permanent magnets (60) that are stacked next to each other within housings (32, 34). In the present example, magnets (60) are completely sealed within beads (30). As best seen in FIG. 4, each bead (30) also defines a chamber (36) that is configured to receive a portion of a respective pair of links (40). Housing (32) defines an opening (32) at one end of chamber (36); while housing (34) defines an opening (35) at the other end of chamber (36).

Each link (40) of the present example comprises a wire (42) that is pre-bent to form an obtuse angle. The free end of each wire (42) terminates in a ball tip (44). Beads (30) are joined together by links (40) such that a first end portion of a link (40) is in one bead (30), a second end portion of the same link (40) is in another bead (30), and an intermediate portion of the same link (40) is positioned between those two beads (30). Chambers (36) of beads (30) are configured to freely receive ball tips (44) and adjacent regions of wires (42); while openings (33, 35) are configured to prevent ball tips (44) from exiting chambers (36). Openings (33, 35) are nevertheless sized to allow wire (42) to slide through openings (33, 35). Thus, links (40) and beads (30) are configured to allow beads (30) to slide along lengths (40) through a restricted range of motion.

Figure 5A:
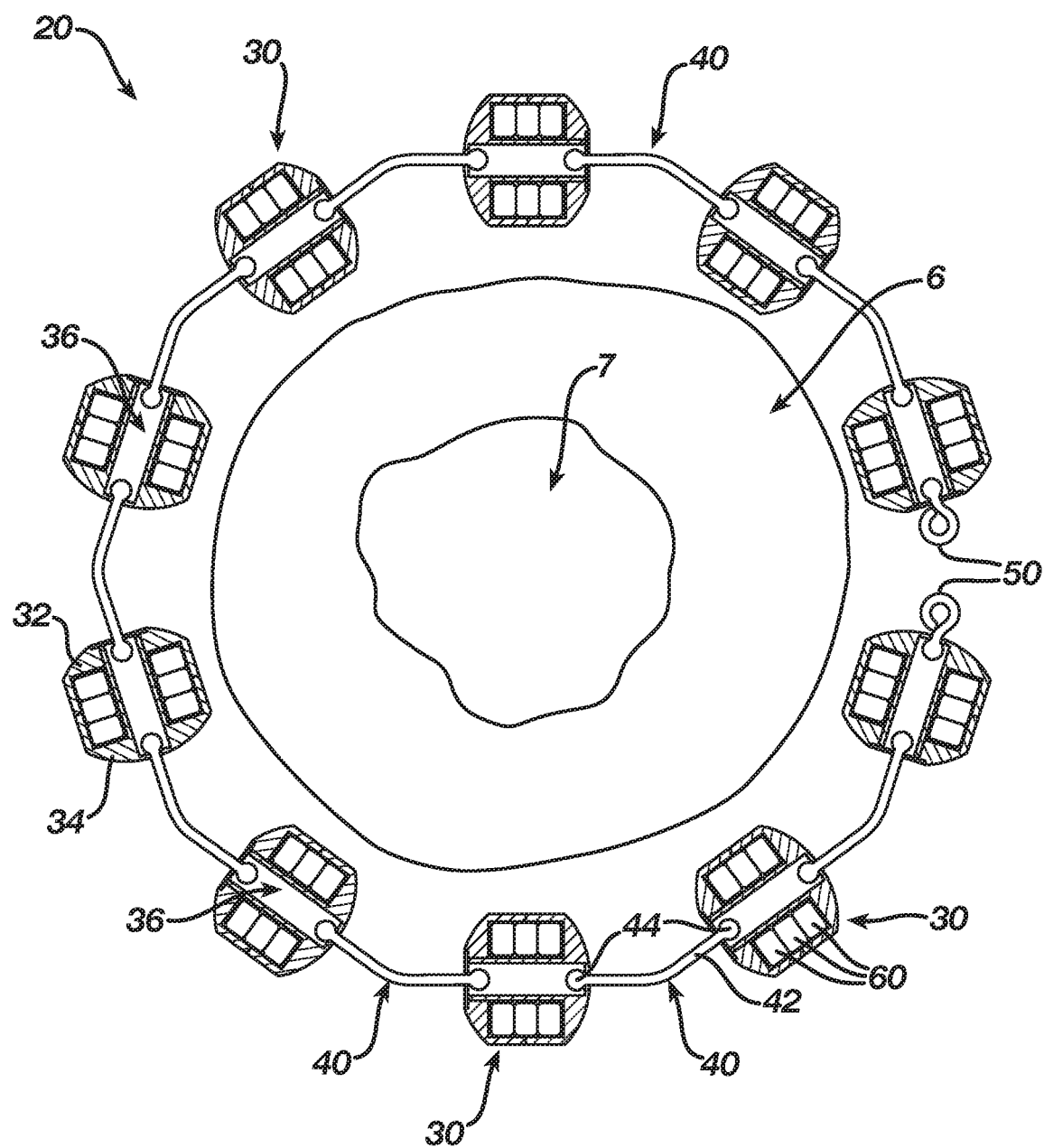
FIG. 5A depicts a top, cross-sectional view of the sphincter augmentation device of FIG. 3 positioned about an LES, with the sphincter augmentation device in an open and expanded configuration.
Figure 5B:
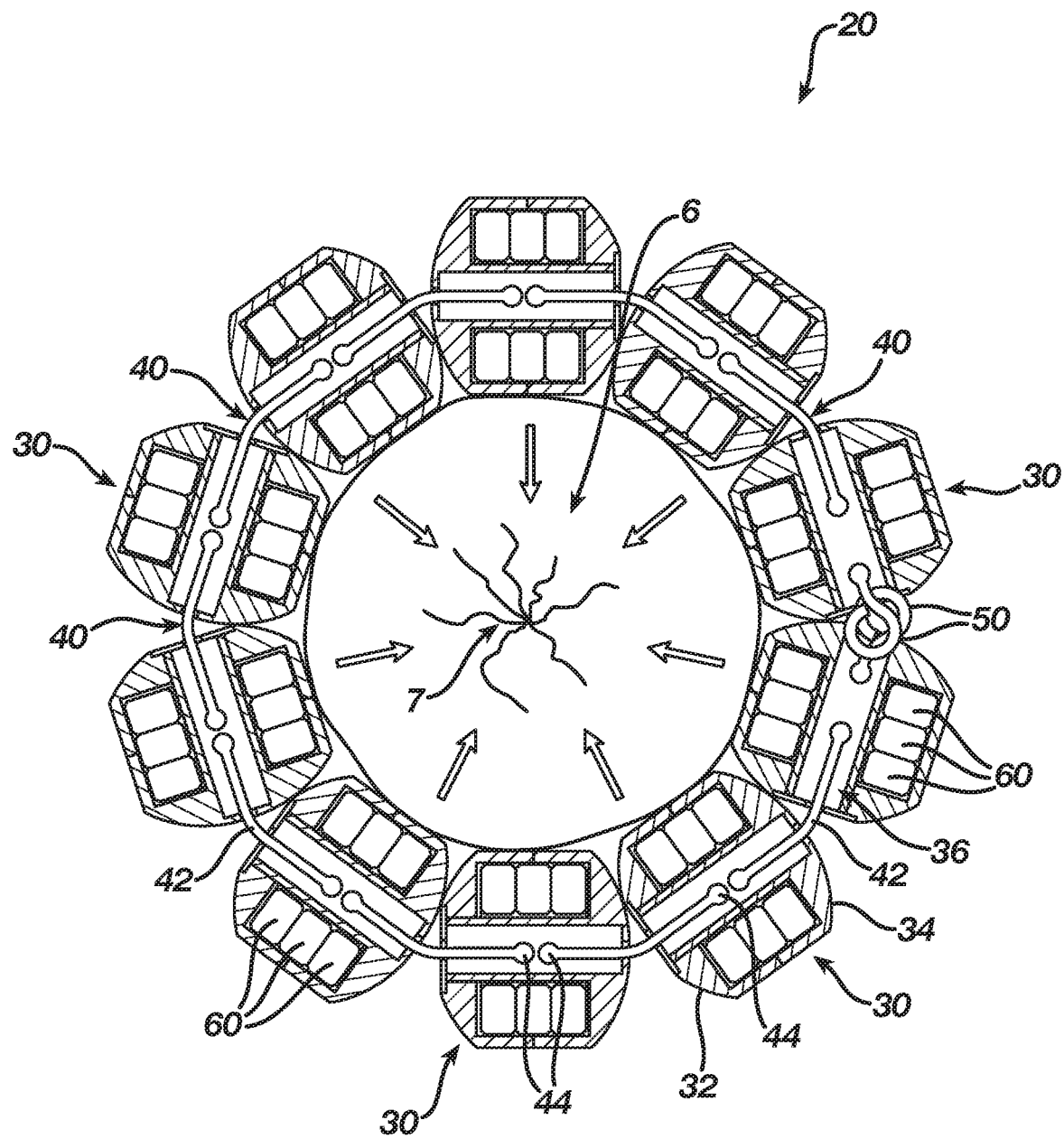
FIG. 5B depicts a top, cross-sectional view of the sphincter augmentation device of FIG. 3 positioned about the LES of FIG. 5A, with the sphincter augmentation device in a closed and contracted configuration.

As best seen in FIGS. 5A-5B, two beads (30) have opposing fastener features (50) that allow the ends of device (20) to be coupled together to form a loop. In the present example, fastener features (50) comprise eyelets. In some other versions, fastener features (50) comprise complementary clasp features, such as those described in greater detail below. As another merely illustrative example, fastener features (50) may be configured and operable in accordance with one or more of the teachings of U.S. patent application Ser. No. 15/664,665, entitled "Method for Assisting a Sphincter," filed Jul. 31, 2017, issued as U.S. Pat. No. 10,405,865 on Sep. 10, 2019, the disclosure of which is incorporated by reference herein. Other suitable ways in which the ends of device (20) may be coupled together to form a loop will be apparent to those of ordinary skill in the art in view of the teachings herein. Those of ordinary skill in the art will also recognize that it may be desirable to provide fastener features (50) that can be decoupled if it becomes necessary or otherwise warranted to remove device (20) from the patient.

FIG. 5A shows device (20) in an open, expanded state, with device (20) being positioned about LES (6). At this stage, the opening (7) defined by LES (6) is in a persistently open state (e.g., allowing the patient to undesirably experience GERD and/or other undesirable conditions), warranting the securement of device (20) about the LES (6). FIG. 5B shows device (20) secured about the LES (6), with device (20) in a closed, contracted state. Device (20) is secured closed via fastener features (50). Magnets (60) are oriented within beads (30) such that each bead (30) will be magnetically attracted to the adjacent bead (30) in device (20). In other words, beads (30) are magnetically attracted to each other to magnetically bias device (20) toward the contracted configuration shown in FIG. 5B.

With device (20) secured around the LES (6) and in the contracted configuration, device (20) deforms the LES (6) radially inwardly to substantially close the opening defined by the LES (6). In doing so, device (20) prevents the patient from experiencing GERD and/or other undesirable conditions that may be associated with a persistently open opening (7) at the LES (6). While magnets (60) have a tesla value that is high enough to substantially maintain opening (7) in a closed state to the point of preventing GERD and/or other undesirable conditions that may be associated with a persistently open opening (7), the tesla value of magnets (60) is low enough to allow LES (6) to expand radially outwardly to accommodate passage of a bolus of food, vomit, etc. through the opening (7) of LES (6). To accommodate such expansion, beads (30) may simply slide along links (40) to enlarge the effective diameter of device (20) as the bolus passes. After the bolus passes, the magnetic bias of magnets (60) will return device (20) to the contracted state shown in FIG. 5B. Device (20) thus ultimately prevents GERD and/or other undesirable conditions that may be associated with a persistently open opening (7); while still permitting the normal passage of food, etc. from the esophagus (2) to the stomach (4).

In addition to the foregoing, device (20) may be constructed and operable in accordance with at least some of the teachings of U.S. Pat. No. 7,695,427, the disclosure of which is incorporated by reference herein; and/or U.S. patent application Ser. No. 15/664,665, entitled "Method for Assisting a Sphincter," filed Jul. 31, 2017, issued as U.S. Pat. No. 10,405,865 on Sep. 10, 2019, the disclosure of which is incorporated by reference herein.

Figure 6:
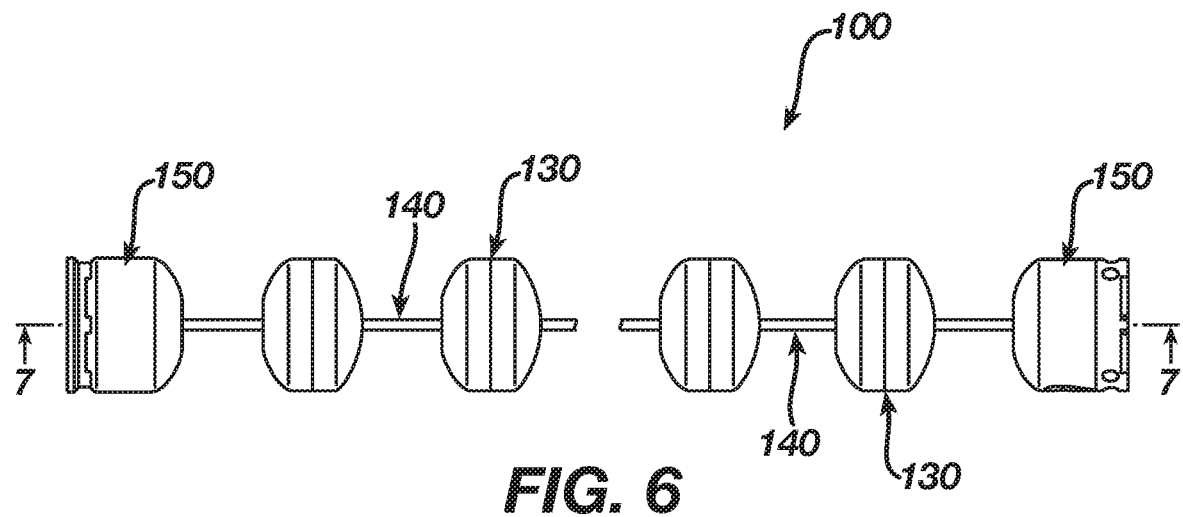
FIG. 6 depicts a top plan view of an exemplary alternative sphincter augmentation device, with the sphincter augmentation device in an open, linear configuration.
Figure 7:
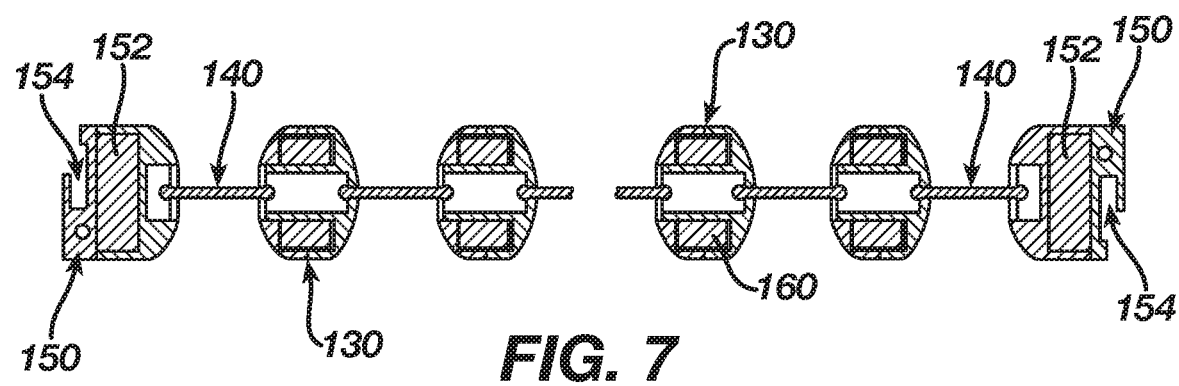
FIG. 7 depicts a cross-sectional view of the sphincter augmentation device of FIG. 6, taken along line 7-7 of FIG. 6.

FIGS. 6-7 show another exemplary variation of device (20). In particular, FIGS. 6-7 show a sphincter augmentation device (100) that comprises a plurality of beads (130) and corresponding links (140). Links (140) secure beads (130) together and are slidably disposed relative to beads (130), such that the effective length of device (100) is variable. Each bead (130) contains a magnet (160). Magnets (160) provide magnetic attraction between adjacent beads (130), such that beads (130) are magnetically biased toward each other along links (140). Device (100) of this example also includes a pair of clasp members (150) at each end of device (100). Each clasp member (150) also includes a respective magnet (152) and a clasp feature (154). Magnets (152) are configured to magnetically bias clasp members (150) toward each other. Clasp features (154) are configured to releasably mechanically secure clasp members (150) to each other. Various suitable structures that may be used to form clasp features (154) will be apparent to those of ordinary skill in the art in view of the teachings herein.

Device (100) may be used in a manner similar to device (20), with clasp members (150) essentially serving as substitutes for fastener features (50). An operator may thus wrap device (100) around an LES (6) and secure clasp members (150) to each other. Magnets (152, 160) may cooperate to urge the LES (6) toward a contracted configuration (e.g., like the configuration shown in FIG. 5B); yet beads (130) may still slide along links (140) to allow the LES (6) to expand to thereby allow a bolus of food or vomit, etc., to pass through the LES (6).

II. EXEMPLARY FEATURES AND METHODS TO ADJUST SPHINCTER AUGMENTATION DEVICE

Each sphincter augmentation device (20, 100) described above is capable of changing its effective length as beads (30, 130) slide along links (40, 140), thereby providing a variable circumference to accommodate a bolus of food or vomit, etc., passing through the LES (6). However, some patients may encounter dysphagia when a device (20, 100) is installed around their LES (6). This dysphagia may make it difficult for the patient to swallow or provide other undesirable results. This dysphagia may occur for various reasons. By way of example only, some patients may grow scar tissue on the tissue adjacent to device (20, 100). In such cases, even if device (20, 100) is functioning properly and the patient does not encounter dysphagia immediately after device (20, 100) is installed, the buildup of scar tissue may eventually result in dysphagia. Alternatively, dysphagia may occur for reasons other than buildup of scar tissue.

It may therefore be desirable to provide a feature or method to adjust the restriction provided by device (20, 100), thereby relieving the dysphagia while still preventing GERD and/or other conditions that may be associated with a malfunctioning LES (6). The following describes various examples of features and methods that may be used to adjust the restriction provided by device (20, 100). The below-described features and methods may be used after device (20, 100) has been installed around the LES (6), without needing to remove device (20, 100) from the LES (6).

A. Exemplary Adjustable Clasp Members for Sphincter Augmentation Device

Figure 8:
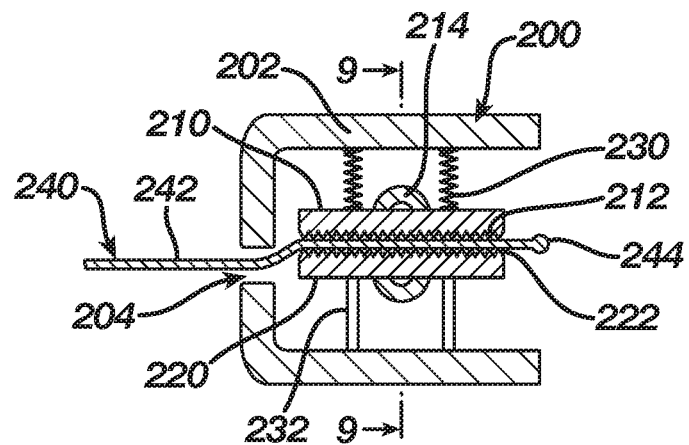
FIG. 8 depicts a cross-sectional side view of an exemplary clasp member that may be incorporated into the sphincter augmentation devices of FIGS. 3 and 6.
Figure 9A:
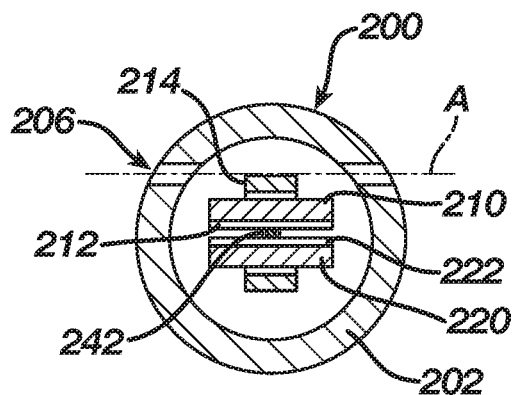
FIG. 9A depicts a cross-sectional view of the clasp member of FIG. 8, taken along line 9-9 of FIG. 8, with a clamping assembly clamping a link of the clasp member.
Figure 9B:
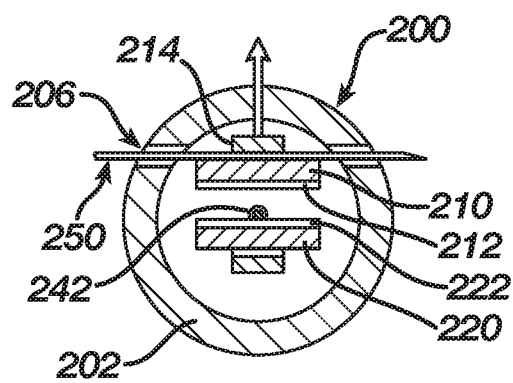
FIG. 9B depicts a cross-sectional view of the clasp member of FIG. 8, taken along line 9-9 of FIG. 8, with a needle inserted into the clasp member to release the link from the clamping assembly.

FIGS. 8-9B show an exemplary clasp member (200) that may be incorporated into device (20) in place of fastener feature (50); or in device (100) in place of clasp member (150). While only one clasp member (200) is shown, variations of devices (20, 100) may include two clasp members (200), with each clasp member (200) being positioned at a respective free end of device (20, 100). Clasp member (200) may thus include features enabling clasp member (200) to be removably secured to another clasp member (200). For instance, clasp member (200) may include a structure like clasp feature (154). In still other variations, a device (20, 100) may have one clasp member (200) at one free end of device (20, 100) and a clasp member (150) at the other free end of device (20, 100), with clasp members (150, 200) being configured to removably couple with each other. Still other suitable ways in which clasp member (200) may removably couple with another clasp member in order to provide a sphincter augmentation device with a closed-loop configuration will be apparent to those of ordinary skill in the art in view of the teachings herein.

As shown in FIG. 8, clasp member (200) of this example includes a housing (202) containing a first clamp plate (210) and a second clamp plate (220). Clamp plates (210, 220) are positioned to capture a link (240), which comprises a wire (242) and a ball tip (244). Wire (242) is slidably disposed in an opening (204) formed by housing (202). While not shown, the other end of link (240) is coupled with a bead such as bead (30, 130). Each clamp plate (210, 220) includes a respective clamping surface (212, 222) that is positioned to engage wire (242). First clamp plate (210) is coupled with housing (202) via resilient members (230), which are configured to resiliently urge first plate (210) toward wire (242) and second clamp plate (220). By way of example only, resilient members (230) may comprise coil springs, leaf springs, fluid bladders, elastomeric members, etc. Second clamp plate (210) is coupled with housing (202) via rigid bosses (232).

Clamping surfaces (212, 222) are configured to cooperate to grip wire (242). In the present example, each clamping surface (212, 222) includes a set of ridges that are configured to promote gripping of wire (242). Alternatively, any other suitable kind of structures (e.g., knurling, grit, elastomeric features, etc.) may be used to promote gripping of wire (242). In some versions, the region of wire (242) between clamping surfaces (212, 222) also includes surface features (e.g., knurling, ridges, etc.) that promote gripping engagement between wire (242) and clamping surfaces (212, 222). Also in some versions, the gripping force of clamping surfaces (212, 222) on wire (242) is just slightly higher than the force that is required to maintain functionality of device (20) in urging LES (6) to a substantially closed configuration. In some such versions, the effective diameter of device (20) may be enlarged by pulling clasp member (200) away from an adjacent bead (30), thereby sliding clasp member (200) along wire (242). Such an adjustment pulling force may exceed the force imposed at the interface of clamping surfaces (212, 222) and wire (242) during normal passage of a bolus of food, vomit, etc., through opening (7) of LES (6).

As shown in FIGS. 9A-9B, housing (202) defines a pair of transverse openings (206) that are offset from the center of housing (202). Openings (206) are aligned with each other along an axis (A). As shown in FIGS. 8-9B, first clamp plate (210) also includes an upper loop structure (214). As shown in FIG. 9A, upper loop structure (214) is offset from the axis (A) when first plate (212) is engaged with wire (242). However, as shown in FIG. 9B, an operator may pass a needle (250) (or pin or other structure) through opening (206), then through upper loop structure (214), and thereby urge first clamp plate (210) away from wire (242) and second clamp plate (220). This will release wire (242) from the grip between clamp plates (210, 220), thereby allowing wire (242) to slide relative to housing (202). Ball tip (244) is sized larger than opening (204), thereby preventing ball tip (244) from inadvertently exiting through opening (204).

In the present example, only clamp plate (210) is configured to be engaged by a needle (250) and then be moved by needle (250). In some other versions, clamp plate (220) is also configured to be engaged by a needle (250) and then be moved by needle (250). In such versions, housing (202) may include an additional pair of transverse openings (206) to allow needle (250) to engage a loop structure (e.g., like loop structure (214)) of clamp plate (220).

Figure 10A:
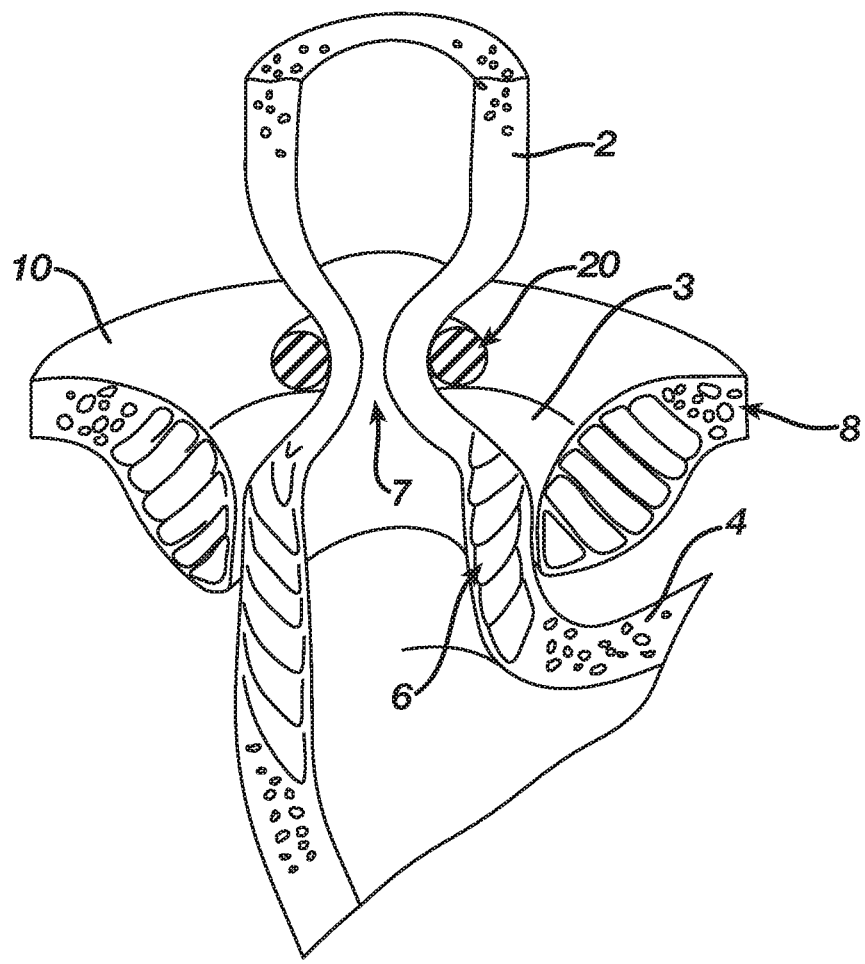
FIG. 10A depicts a cross-sectional isometric view, taken along a coronal plane of the body, of a human esophago-gastric junction, with a sphincter augmentation device positioned about the esophagus to provide a restricted opening at the esophago-gastric junction.
Figure 10B:
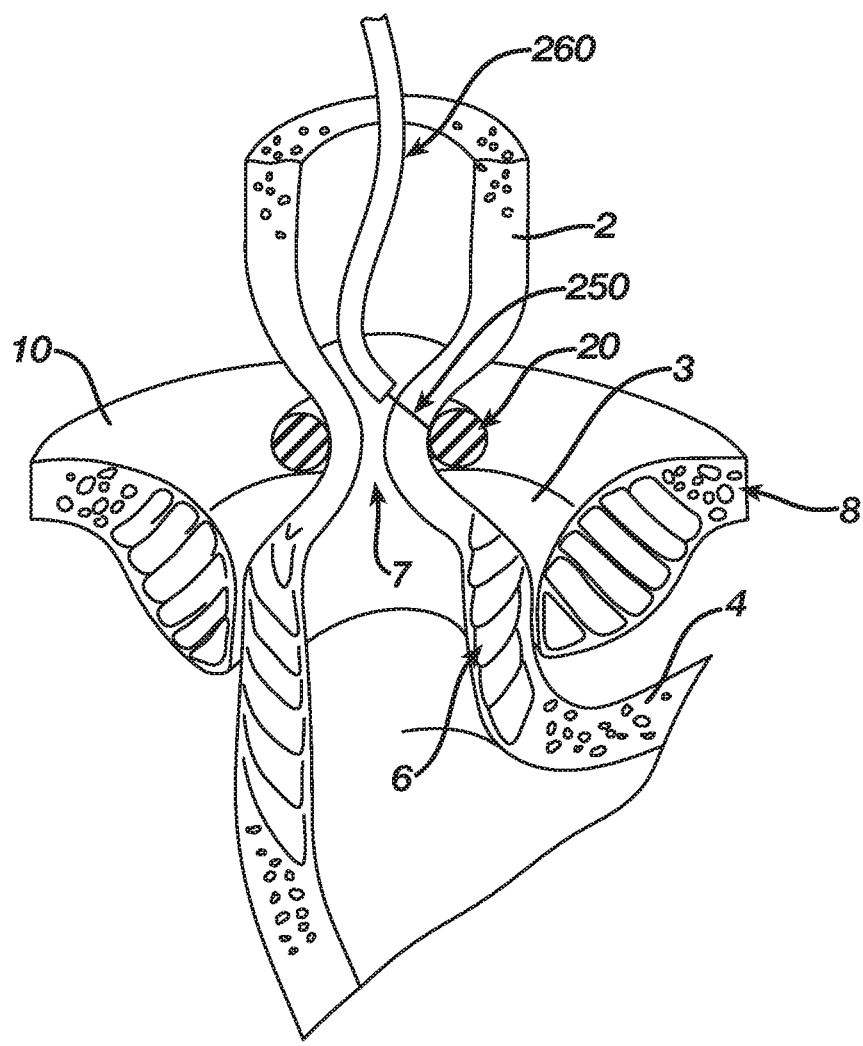
FIG. 10B depicts a cross-sectional isometric view, taken along a coronal plane of the body, of a human esophago-gastric junction, with a sphincter augmentation device positioned about the esophagus, with an endoscope transorally inserted into the esophagus, and with a needle passing through the wall of the esophagus to engage a clasp member of the sphincter augmentation device and thereby adjust the sphincter augmentation device.
Figure 10C:
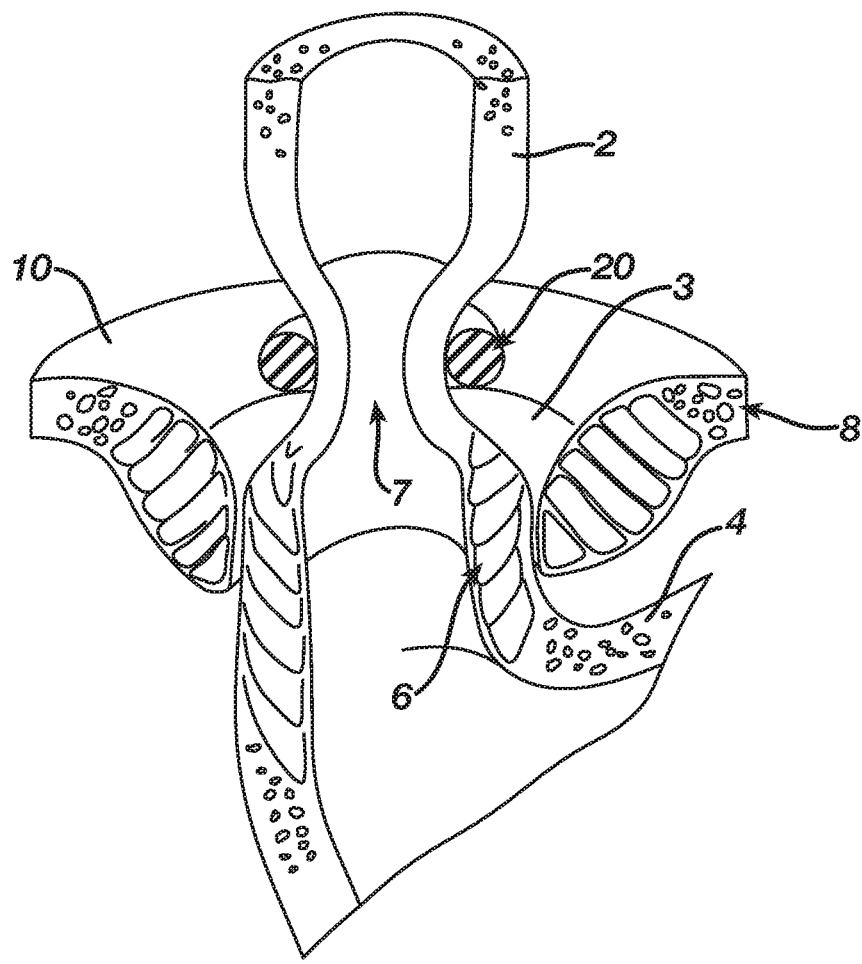
FIG. 10C depicts a cross-sectional isometric view, taken along a coronal plane of the body, of a human esophago-gastric junction, with a sphincter augmentation device positioned about the esophagus to provide a restricted opening at the esophago-gastric junction, with the restricted opening being enlarged relative to the restricted opening of FIG. 10A due to the adjustment of FIG. 10B.

FIGS. 10A-10C show an exemplary use of a device (20) containing a clasp member (200). In FIG. 10A, device (20) is installed at the LES (6) in an initial state, providing a restricted opening (7) in the LES (6). In this state, the patient is experiencing dysphagia, warranting an adjustment of the effective circumference of device (20). To provide this adjustment, an endoscope (260) is introduced transorally into the esophagus, with the distal end of the endoscope (260) being positioned in the region of the esophagus (2) adjacent to device (20). Needle (250) is advanced distally from the distal end of the endoscope (260), through the wall of the esophagus (2), to reach clasp member (200). In particular, needle (250) is advanced through opening (206), then through upper loop structure (214). Needle (250) is then used to urge first clamp plate (210) away from wire (242) and second clamp plate (220). This releases the grip of clamp plates (210, 220) on wire (242), as shown in FIG. 9B, allowing a portion of wire (242) to slide out of housing (202). This enlarges the effective circumference of device (20). After providing this enlargement, needle (250) is pulled from upper loop structure (214) and housing (202). Resilient members (230) then return clamp plate (210) to the position shown in FIGS. 8 and 9A, such that clamp plate (210) is returned into engagement with wire (242). Clamp plates (210, 220) thus cooperate to maintain wire (242) in the adjusted position relative to housing (202).

FIG. 10C shows an enlarged opening (7) after device (20) has been adjusted as described above. While opening (7) is shown in an open state in FIGS. 10A-10C, opening (7) may in fact be in a closed state during all of these stages. However, the restrictive force provided by device (20) may be reduced in the stage shown in FIG. 10C as compared to the stage shown in FIG. 10A. In other words, it will be easier for a bolus of food, vomit, etc. to pass through opening (7) after the stage shown in FIG. 10C than in the stage shown in FIG. 10A, due to the slightly enlarged effective diameter of device (20). Thus, opening (7) is shown as being open throughout the FIG. 10A-10C series to schematically illustrate the slightly relaxed constriction by device (20).

While FIG. 10B shows clasp member (200) being engaged by needle (250) from a transesophageal approach, clasp member (200) may instead be engaged from outside the esophagus. For instance, an instrument may be introduced from a thoracic approach, or otherwise, to engage clasp member (200) with a needle (250) without passing needle (250) through the esophagus (2). Other suitable ways in which needle (250) may be inserted into clasp member (200) will be apparent to those of ordinary skill in the art in view of the teachings herein.

When the grip of clamp plates (210, 220) on wire (242) is relieved as described above, the operator may rely on an outward bias provided by the LES (6) to expand the effective circumference of device (20) before releasing clamp plate (210) to re-clamp wire (242) between clamp plates (210, 220). Alternatively, device (20) may be grasped with one or more conventional grasping instruments to controllably adjust the effective circumference of device (20) before releasing clamp plate (210) to re-clamp wire (242) between clamp plates (210, 220). In instances where the operator wishes to reduce the effective circumference of device (20), the operator may push wire (242) further into housing (202) while the grip of clamp plates (210, 220) on wire (242) is relieved as described above. Wire (242) may have sufficient column strength to tolerate such pushing. Again, once a desired amount of wire (242) has been pushed into housing (202), clamp plate (210) may be released to re-clamp wire (242) between clamp plates (210, 220).

While clamp plates (210, 220) are described as being incorporated in clasp members (200) in the present example, clamp plates (210, 220) may be incorporated into one or more beads (30), in addition to or as an alternative to clamp plates (210, 220) being incorporated into clasp members (200).

Figure 11A:
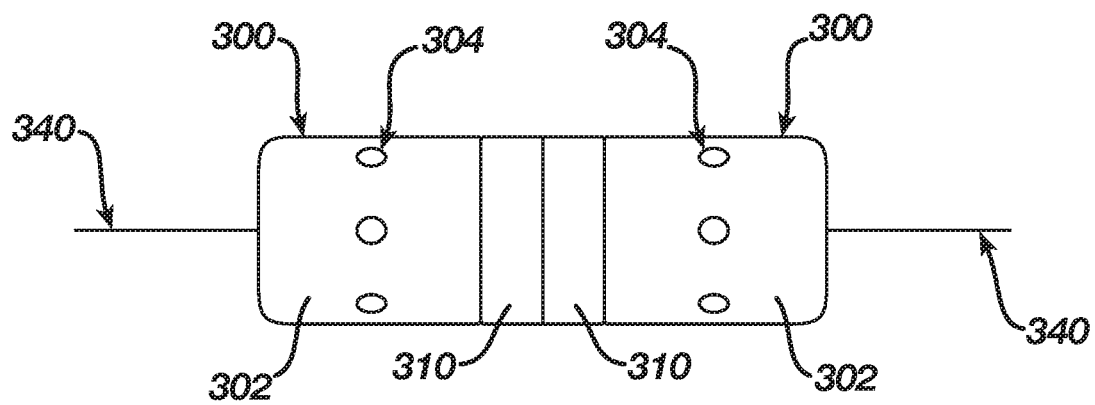
FIG. 11A depicts a side elevational view of a pair of exemplary clasp members that may be incorporated into the sphincter augmentation devices of FIGS. 3 and 6, with the clasp members secured together, and with the clasp members in respective first positions.
Figure 11B:
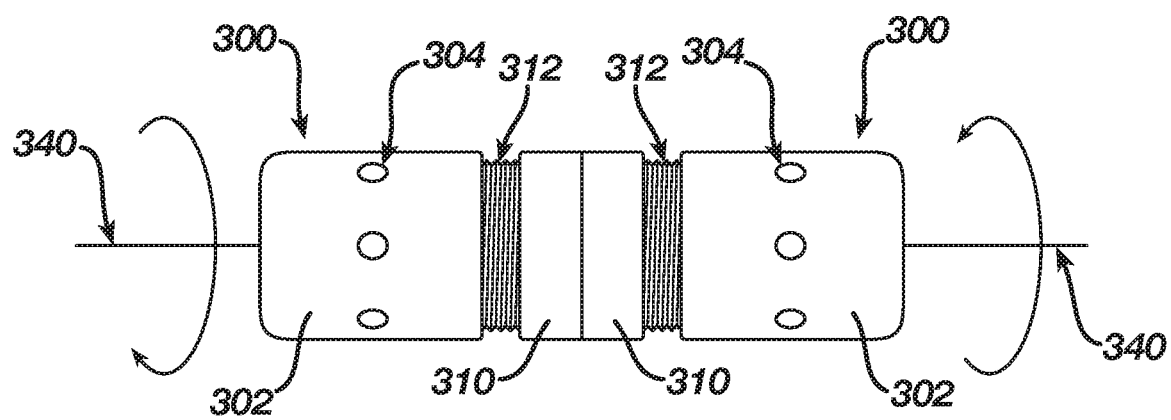
FIG. 11B depicts a side elevational view of the clasp members of FIG. 11A, with the clasp members secured together, and with the clasp members in respective second positions.

FIGS. 11A-11B show another exemplary clasp member (300) that may be incorporated into device (20) in place of fastener feature (50); or in device (100) in place of clasp member (150). Clasp member (300) of this example includes a housing (302) that defines an angularly spaced array of openings (304). Clasp member (300) also includes a coupling feature (310) with a threaded feature (312) that provides threaded engagement between coupling feature (310) and housing (302). As shown, coupling feature (310) is configured to removably couple with another coupling feature (310) of another clasp member (300). By way of example only, coupling features (310) may include complementary structures similar to clasp feature (154). Other suitable ways in which coupling features (310) may removably couple together will be apparent to those of ordinary skill in the art in view of the teachings herein.

Links (340) extend outwardly from each clasp member (300), opposite to coupling features (310). While not shown, the other end of each link (340) is coupled with a bead such as bead (30, 130). Clasp members (300) may thus be coupled together via coupling features (310) to form a closed loop configuration with beads (30, 130) around an LES (6), similar to devices (20, 200) described above. In instances where an operator wishes to adjust the effective circumference of a device incorporating clasp members (300), the operator may rotate clasp members (300) about respective longitudinal axes. As shown in FIG. 11B, this rotation will provide translation of coupling features (310) relative to housings (302), due the threaded engagement of threaded features (312). As housings (302) are urged apart from each other due to this translation, the effective circumference of a device incorporating clasp members (300) will be enlarged.

In the present example, the rotation of housings (302) about the longitudinal axis is accomplished by inserting a needle or pin in opening (304) and then using such a needle or pin to rotate housings (302) in opposite angular directions relative to each other (or at least holding one housing (302) stationary while rotating the other housing (302)). In some instances, the operator may insert a needle/pin/etc. in one opening (304), rotate housing (302) through a first range of angular motion, remove the needle/pin/etc. from opening (304), insert the needle/pin/etc. in another opening (304), rotate housing (302) through a second range of angular motion, and repeat this process as many times as needed until housing (302) has been rotated through a desired angular range. In some other versions, each housing (302) includes a set of flats or other features that may be engaged by a wrench, grasping instrument, or other tool to rotate at least one of housings (302) relative to the other housing (302). Various suitable structures, techniques, and tools that may be used to rotate at least one of housings (302) relative to the other housing (302) will be apparent to those of ordinary skill in the art in view of the teachings herein.

B. Exemplary Use of Magnets to Adjust Sphincter Augmentation Device

In some scenarios, a sphincter augmentation device (20, 200) may lack features that provide selective adjustment of the effective length/circumference of device (20, 200). As an alternative to providing mechanical adjustment of device (20, 200), device (20, 200) may be exposed to a strong magnetic field that reduces the magnetic strength of magnets (60, 160). Reducing the magnetic strength of magnets (60, 160) will reduce the strength of attraction between adjacent beads (30, 130), which will in turn reduce the strength of the radially inward forces exerted on the LES (6) by device (20, 200). Thus, when a patient with a device (20, 200) installed experiences dysphagia, a method of treatment may include reducing the magnetic strength of magnets (60, 160).

Figure 12A:
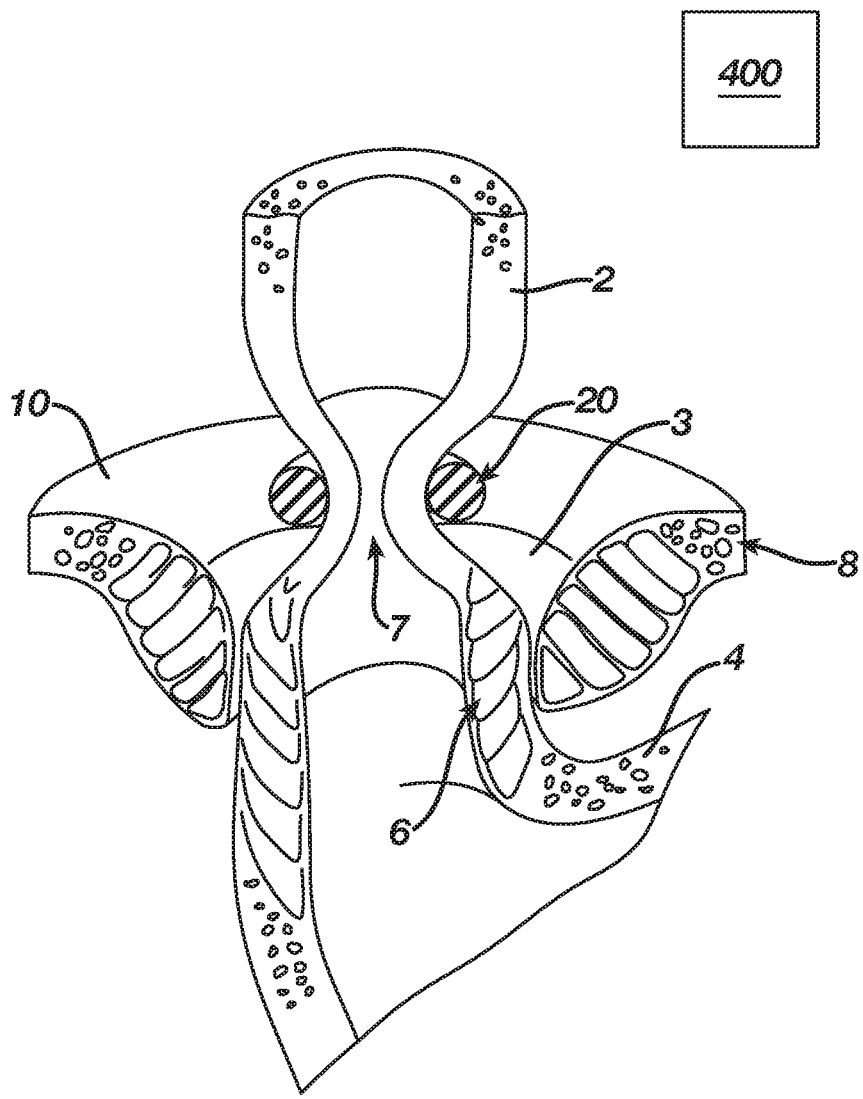
FIG. 12A depicts a cross-sectional isometric view, taken along a coronal plane of the body, of a human esophago-gastric junction, with a sphincter augmentation device positioned about the esophagus to provide a restricted opening at the esophago-gastric junction, and with an external magnetic device in proximity to the sphincter augmentation device.
Figure 12B:
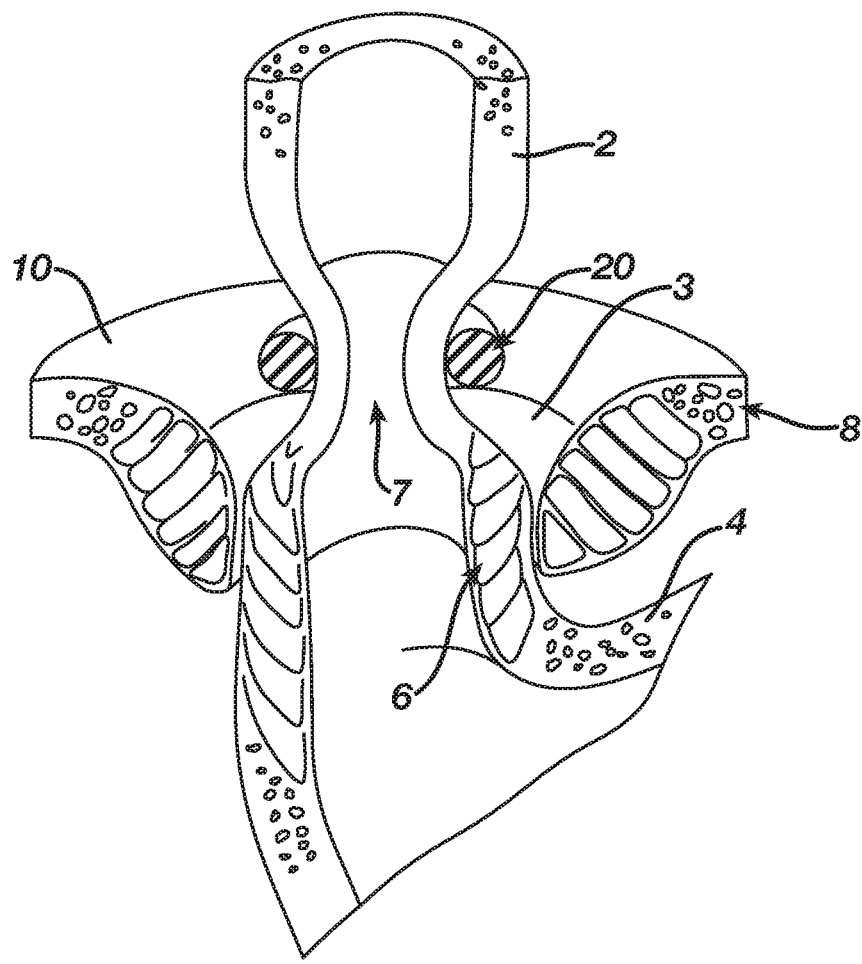
FIG. 12B depicts a cross-sectional isometric view, taken along a coronal plane of the body, of a human esophago-gastric junction, with a sphincter augmentation device positioned about the esophagus to provide a restricted opening at the esophago-gastric junction, with the restricted opening being enlarged relative to the restricted opening of FIG. 12A due to a magnetic field from the external magnetic device of FIG. 12A.

FIGS. 12A-12B show one merely exemplary method of reducing the magnetic strength of magnets (60). In this example, device (20) is exposed to a substantially strong external magnetic field applied from a magnetic device (400), as shown in FIG. 12A. In some versions, magnetic device (400) comprises an MRI machine. In some other versions, magnetic device (400) comprises a substantially powerful permanent magnet or electromagnet that is placed on or over the patient's chest, in a region generally over device (20). Still other suitable forms that external magnetic device (400) may take will be apparent to those of ordinary skill in the art in view of the teachings herein. In the present example, the exposure to the substantially strong external magnetic field applied from magnetic device (400) reduces the magnetic strength of magnets (60).

After sufficient exposure to the strong magnetic field of magnetic device (400), the reduction in the magnetic strength of magnets (60) reduces the strength of attraction between adjacent beads (30), which in turn reduces the strength of the radially inward forces exerted on the LES (6) by device (20). FIG. 12B shows an effectively enlarged opening (7) resulting from the reduction in forces exerted on the LES (6) by device (20). While opening (7) is shown in an open state in FIG. 12B, opening (7) may in fact be in a closed state during both of the stages shown in FIGS. 12A-12B. However, the restrictive force provided by device (20) may be reduced in the stage shown in FIG. 12B as compared to the stage shown in FIG. 12A. In other words, it will be easier for a bolus of food, vomit, etc. to pass through opening (7) after the stage shown in FIG. 12B than in the stage shown in FIG. 12A, due to the slightly enlarged effective diameter of device (20). Thus, opening (7) is shown as being open throughout the FIG. 12A-12B series to schematically illustrate the slightly relaxed constriction by device (20).

In some versions of the method depicted in FIGS. 12A-12B, before device (20) is exposed to the substantially strong external magnetic field applied from magnetic device (400), an operator may insert a trocar or other shaft down the esophagus (2) and thereby position a distal portion of the shaft in the opening (7) of the LES (6). The distal portion of the shaft may be sized to expand the opening (7) and thereby expand device (20) to a state similar to that shown in FIG. 5A. The operator may then expose the patient to the substantially strong external magnetic field from magnetic device (400) as described above. By having the expanding distal portion of the shaft in the opening (7) of the LES (6), the resulting expansion of device (20) may prevent magnets (60) from substantially twisting in response to the substantially strong external magnetic field from magnetic device (400).

Figure 13A:
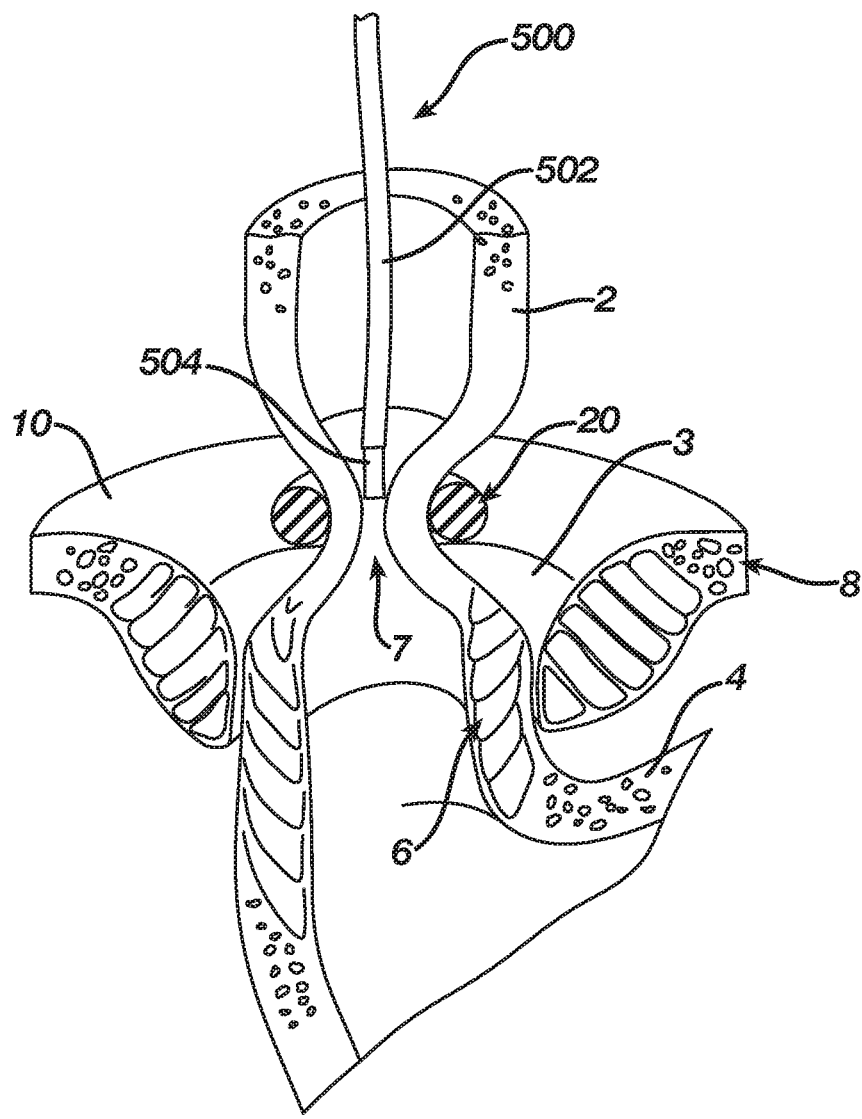
FIG. 13A depicts a cross-sectional isometric view, taken along a coronal plane of the body, of a human esophago-gastric junction, with a sphincter augmentation device positioned about the esophagus to provide a restricted opening at the esophago-gastric junction, and with a permanent magnet instrument transorally inserted into the esophagus and into proximity with the sphincter augmentation device.
Figure 13B:
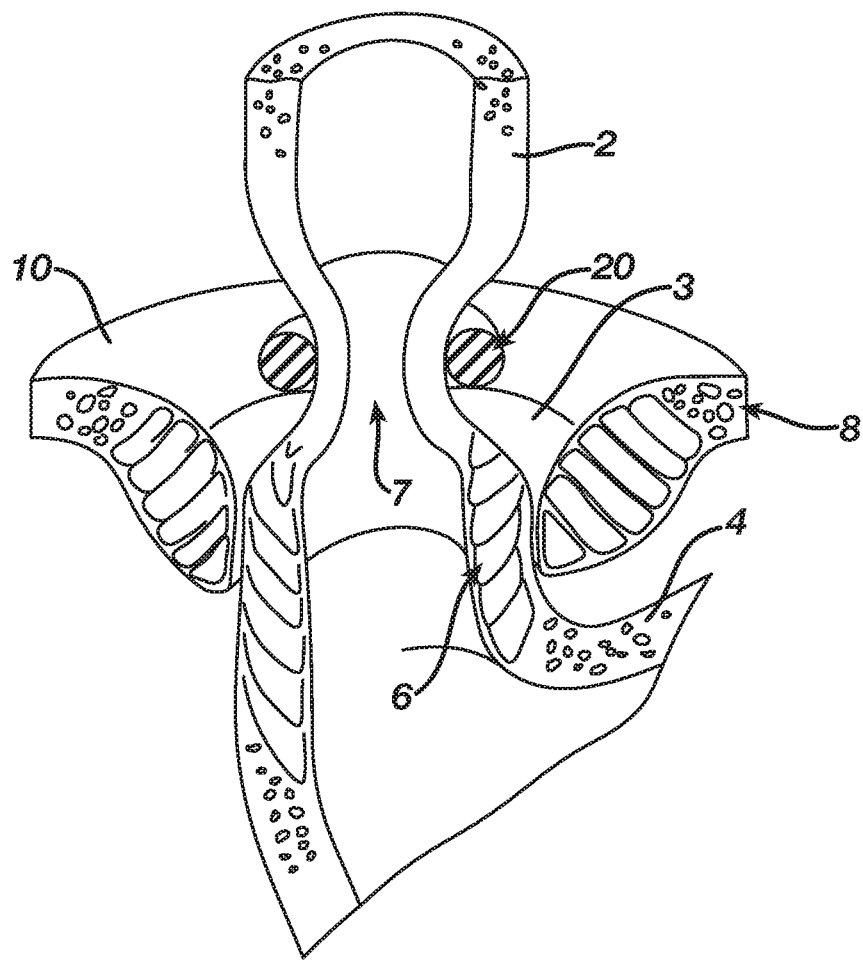
FIG. 13B depicts a cross-sectional isometric view, taken along a coronal plane of the body, of a human esophago-gastric junction, with a sphincter augmentation device positioned about the esophagus to provide a restricted opening at the esophago-gastric junction, with the restricted opening being enlarged relative to the restricted opening of FIG. 13A due to a magnetic field from the permanent magnet instrument of FIG. 13A.

FIGS. 13A-13B show another exemplary method of reducing the magnetic strength of magnets (60). In this example, an instrument (500) is inserted transorally into the esophagus (2). Instrument (500) includes an elongate shaft (502) with a substantially strong permanent magnet (504) positioned at the distal end of shaft (502). As shown in FIG. 13A, instrument (500) is inserted to a depth sufficient to position magnet (504) near the region of the LES (6) associated with device (20), thereby exposing magnets (60) to the substantially strong magnetic field of magnet (504). In the present example, the exposure to the substantially strong external magnetic field from magnet (504) reduces the magnetic strength of magnets (60).

After sufficient exposure to the strong magnetic field of magnet (504), the reduction in the magnetic strength of magnets (60) reduces the strength of attraction between adjacent beads (30), which in turn reduces the strength of the radially inward forces exerted on the LES (6) by device (20). FIG. 13B shows an effectively enlarged opening (7) resulting from the reduction in forces exerted on the LES (6) by device (20). While opening (7) is shown in an open state in FIG. 13B, opening (7) may in fact be in a closed state during both of the stages shown in FIGS. 13A-13B. However, the restrictive force provided by device (20) may be reduced in the stage shown in FIG. 13B as compared to the stage shown in FIG. 13A. In other words, it will be easier for a bolus of food, vomit, etc. to pass through opening (7) after the stage shown in FIG. 13B than in the stage shown in FIG. 13A, due to the slightly enlarged effective diameter of device (20). Thus, opening (7) is shown as being open throughout the FIG. 13A-13B series to schematically illustrate the slightly relaxed constriction by device (20).

Figure 14A:
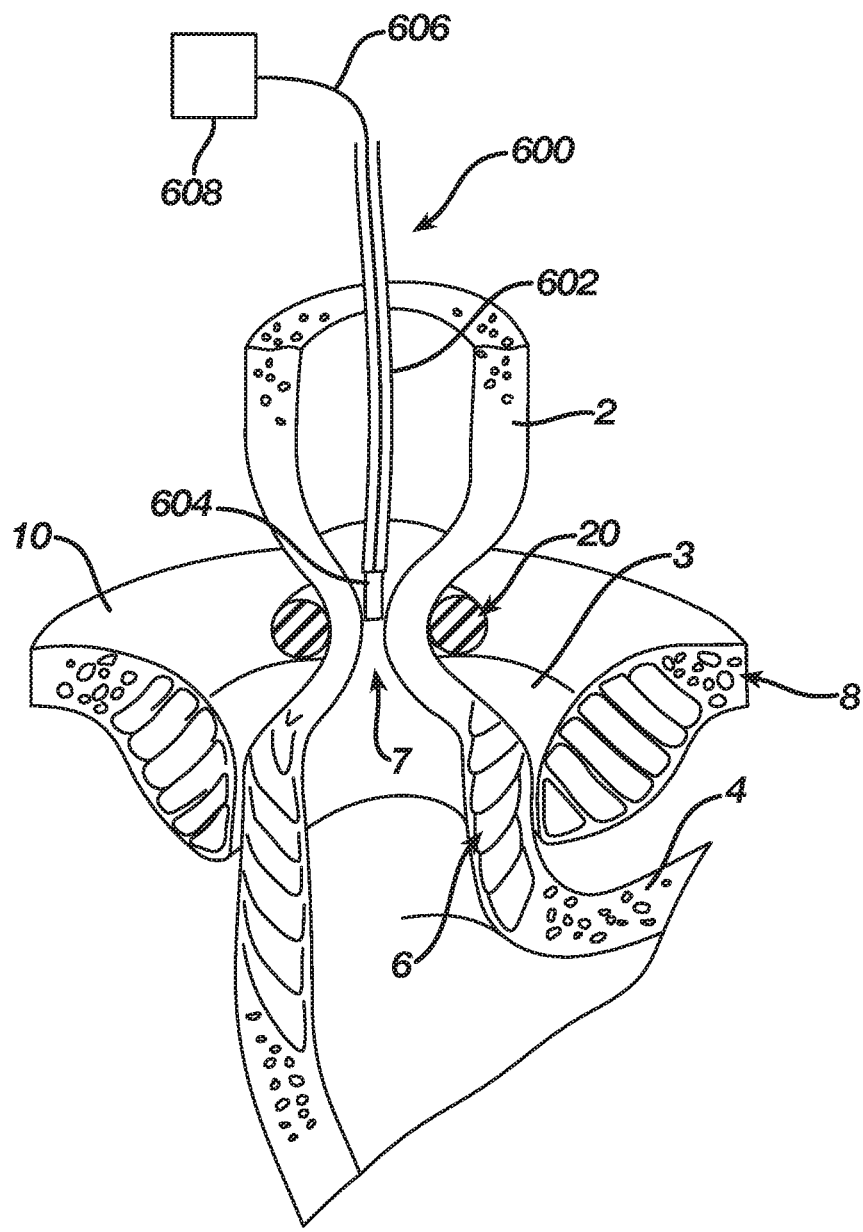
FIG. 14A depicts a cross-sectional isometric view, taken along a coronal plane of the body, of a human esophago-gastric junction, with a sphincter augmentation device positioned about the esophagus to provide a restricted opening at the esophago-gastric junction, and with an electromagnet instrument transorally inserted into the esophagus and into proximity with the sphincter augmentation device.
Figure 14B:
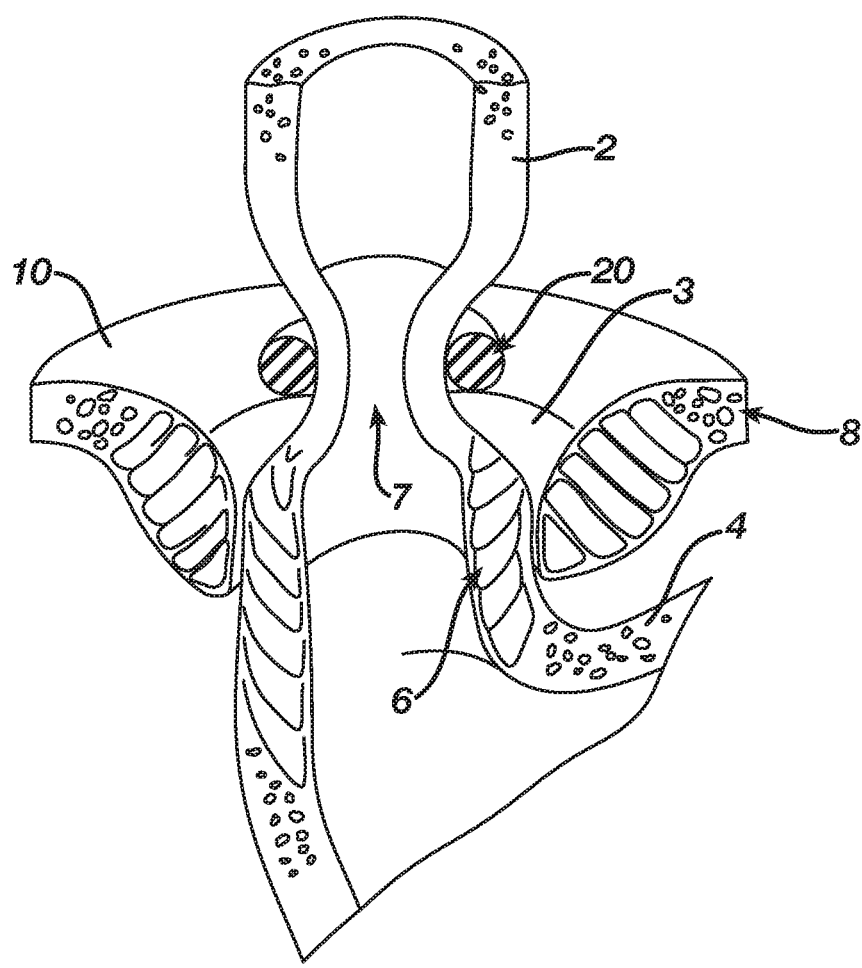
FIG. 14B depicts a cross-sectional isometric view, taken along a coronal plane of the body, of a human esophago-gastric junction, with a sphincter augmentation device positioned about the esophagus to provide a restricted opening at the esophago-gastric junction, with the restricted opening being enlarged relative to the restricted opening of FIG. 14A due to a magnetic field from the electromagnet instrument of FIG. 14A.

FIGS. 14A-14B show another exemplary method of reducing the magnetic strength of magnets (60). In this example, an instrument (600) is inserted transorally into the esophagus (2). Instrument (600) includes an elongate shaft (602) with an electromagnetic head (604) positioned at the distal end of shaft (602). Electromagnetic head (604) is coupled with a power source (608) via a wire (606). When power source (608) is activated, electromagnetic head (604) generates a substantially strong electromagnetic field. As shown in FIG. 14A, instrument (600) is inserted to a depth sufficient to position electromagnetic head (604) near the region of the LES (6) associated with device (20). Power source (608) is activated, thereby exposing magnets (60) to the substantially strong electromagnetic field of electromagnetic head (604). In the present example, the exposure to the substantially strong external electromagnetic field from electromagnetic head (604) reduces the magnetic strength of magnets (60).

After sufficient exposure to the strong electromagnetic field of electromagnetic head (604), the reduction in the magnetic strength of magnets (60) reduces the strength of attraction between adjacent beads (30), which in turn reduces the strength of the radially inward forces exerted on the LES (6) by device (20). FIG. 14B shows an effectively enlarged opening (7) resulting from the reduction in forces exerted on the LES (6) by device (20). While opening (7) is shown in an open state in FIG. 14B, opening (7) may in fact be in a closed state during both of the stages shown in FIGS. 14A-14B. However, the restrictive force provided by device (20) may be reduced in the stage shown in FIG. 14B as compared to the stage shown in FIG. 14A. In other words, it will be easier for a bolus of food, vomit, etc. to pass through opening (7) after the stage shown in FIG. 14B than in the stage shown in FIG. 14A, due to the slightly enlarged effective diameter of device (20). Thus, opening (7) is shown as being open throughout the FIG. 14A-14B series to schematically illustrate the slightly relaxed constriction by device (20).

While several illustrative examples of devices and techniques for exposing magnets (60, 160) to magnetic fields that are strong enough to reduce the magnetic strength of magnets (60, 160) have been described above, other examples will be apparent to those of ordinary skill in the art in view of the teachings herein. In addition, suitable tesla values for magnets/electromagnets that are used to reduce the magnetic strength of magnets (60, 160) will be apparent to those of ordinary skill in the art in view of the teachings herein. Similarly, suitable exposure durations for substantially strong magnets/electromagnets to reduce the magnetic strength of magnets (60, 160) will be apparent to those of ordinary skill in the art in view of the teachings herein.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, the apparatus comprising: (a) a plurality of beads, wherein each bead comprises: (i) a housing, (ii) a passageway extending through the housing, and (iii) at least one annular magnet, wherein the at least one annular magnet is coaxially positioned about the passageway; (b) a plurality of links joining the beads together, wherein portions of the links are slidably disposed in corresponding passageways of the beads; (c) a clasp assembly, wherein the clasp assembly is configured to removably secure the beads and links in a loop formation; and (d) an adjustment feature, wherein the adjustment feature is operable to adjust an effective circumference of the loop formation.

Example 2

The apparatus of Example 1, further comprising a clasp link joining the clasp assembly with one of the beads.

Example 3

The apparatus of Example 2, wherein the adjustment member is located in the clasp assembly, wherein the adjustment member comprises a clamping feature operable to selectively clamp the clasp link and thereby grip the clasp link.

Example 4

The apparatus of Example 3, wherein the clasp assembly comprises a housing containing the clamping feature, wherein the clamping feature comprises: (i) a first clamp plate, wherein the first clamp plate, (ii) a resilient member coupling the first clamp plate to the housing, and (iii) a second clamp plate fixedly secured relative to the housing, wherein the clasp link is positioned between the first and second clamp plates.

Example 5

The apparatus of Example 4, wherein the resilient member is configured to resiliently urge the first clamp plate toward the clasp link and the second clamp plate.

Example 6

The apparatus of any one or more of Examples 4 through 5, wherein the first and second clamp plates comprise opposing gripping features, wherein the gripping features are configured to grip the clasp link.

Example 7

The apparatus of Example 6, wherein the gripping features comprise ridges.

Example 8

The apparatus of any one or more of Examples 4 through 7, wherein the first clamp plate comprises a loop, wherein the loop is configured to receive a tool to urge the first clamp plate away from the clasp link and the second clamp plate.

Example 9

The apparatus of Example 8, wherein the housing defines an opening, wherein the opening is configured to provide a path for a tool to pass through the housing and engage the loop of the first clamp plate.

Example 10

The apparatus of any one or more of Examples 8 through 9, wherein the loop is configured to receive a needle to urge the first clamp plate away from the clasp link and the second clamp plate.

Example 11

The apparatus of any one or more of Examples 2 through 10, wherein the clasp link comprises a wire.

Example 12

The apparatus of any one or more of Examples 1 through 11, wherein the clasp assembly comprises a first clasp member and a second clasp member, wherein the first and second clasp member are configured to removably couple with each other to form the loop formation.

Example 13

The apparatus of Example 12, wherein the first clasp member comprises: (i) a first housing, (ii) a first coupling feature, and (iii) a first threaded feature, wherein the first threaded feature provides a threaded coupling between the first housing and the first coupling feature, wherein the first coupling feature is rotatable relative to the first housing to selectively vary a length defined by the combination of the first housing and the first coupling feature; wherein the second clasp member comprises a second coupling feature, wherein the second coupling feature is configured to removably couple with the first coupling feature to thereby selectively secure the first and second clasp members together.

Example 14

The apparatus of Example 13, wherein the second clasp member further comprises: (i) a second housing, and (ii) a second threaded feature, wherein the second threaded feature provides a threaded coupling between the second housing and the second coupling feature, wherein the second coupling feature is rotatable relative to the second housing to selectively vary a length defined by the combination of the second housing and the second coupling feature.

Example 15

The apparatus of any one or more of Examples 13 through 14, wherein the first housing further defines an opening, wherein the opening is configured to receive a needle to thereby permit the needle to drive rotation of the first housing relative to the first coupling feature.

Example 16

A method of adjusting a restriction on an anatomical structure in a patient, wherein the restriction is provided by an apparatus comprising a plurality of beads joined together by a plurality of links to form a loop, wherein the beads comprise magnets magnetically urging the beads toward each other, wherein the loop is installed around the anatomical structure, the method comprising enlarging an effective circumference of the loop after the loop has been installed around the anatomical structure to form the restriction.

Example 17

The method of Example 16, wherein the apparatus further includes an adjustable clasp, wherein the act of enlarging the effective circumference of the loop comprises mechanically manipulating the adjustable clasp.

Example 18

The method of Example 17, wherein the act of enlarging the effective circumference of the loop comprises exposing the apparatus to a magnetic field sufficient to reduce magnetic strength of the magnets of the apparatus.

Example 19

A method of adjusting a restriction on an anatomical structure in a patient, wherein the restriction is provided by an apparatus comprising a plurality of beads joined together by a plurality of links to form a loop, wherein the beads comprise magnets magnetically urging the beads toward each other, wherein the loop is installed around the anatomical structure, wherein the magnets have a first magnetic strength upon installation of the loop around the anatomical structure, the method comprising exposing the magnets to a magnetic field and thereby reducing the magnetic strength of the magnets to a second magnetic strength after the loop has been installed around the anatomical structure to form the restriction, wherein the second magnetic strength is weaker than the first magnetic strength, wherein the reduction of the magnetic strength of the magnets results in enlargement of an effective circumference of the loop.

Example 20

The method of Example 19, wherein the act of exposing the magnets to a magnetic field and thereby reducing the magnetic strength of the magnets to a second magnetic strength comprises positioning the patient in an MRI machine.

IV. MISCELLANEOUS

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, the apparatus comprising:
   (a) a plurality of beads, wherein each bead comprises:
      (i) a housing,
      (ii) a passageway extending through the housing, and
      (iii) at least one annular magnet, wherein the at least one annular magnet is coaxially positioned about the passageway;
   (b) a plurality of links joining the beads together, wherein portions of the links are slidably disposed in corresponding passageways of the beads;
   (c) a clasp assembly that includes a first clasp member and a second clasp member, wherein the first and second clasp members are configured to removably couple with each other to secure the beads and links in a loop formation;
   (d) a clasp link joining the clasp assembly with one of the beads; and
   (e) an adjustment feature located in the clasp assembly, wherein the adjustment feature is operable to selectively adjust an effective circumference of the apparatus in the loop formation, wherein the adjustment feature comprises a clamping feature operable to selectively clamp the clasp link and thereby grip the clasp link.

2. The apparatus of claim 1, wherein the clasp assembly comprises a clasp assembly housing containing the clamping feature, wherein the clamping feature comprises:
   (i) a first clamp plate,
   (ii) a resilient member coupling the first clamp plate to the clasp assembly housing, and
   (iii) a second clamp plate fixedly secured relative to the clasp assembly housing, wherein the clasp link is positioned between the first and second clamp plates.

3. The apparatus of claim 2, wherein the resilient member is configured to resiliently urge the first clamp plate toward the clasp link and the second clamp plate.

4. The apparatus of claim 2, wherein the first and second clamp plates comprise opposing gripping features, wherein the gripping features are configured to grip the clasp link.

5. The apparatus of claim 4, wherein the gripping features comprise ridges.

6. The apparatus of claim 2, wherein the first clamp plate comprises a loop, wherein the loop is configured to receive a tool to urge the first clamp plate away from the clasp link and the second clamp plate.

7. The apparatus of claim 6, wherein the clasp assembly housing defines an opening, wherein the opening is configured to provide a path for a tool to pass through the clasp assembly housing and engage the loop of the first clamp plate.

8. The apparatus of claim 6, wherein the loop is configured to receive a needle to urge the first clamp plate away from the clasp link and the second clamp plate.

9. An apparatus, the apparatus comprising:
   (a) a plurality of beads, wherein each bead comprises:
      (i) a housing,
      (ii) a passageway extending through the housing, and
      (iii) at least one annular magnet, wherein the at least one annular magnet is coaxially positioned about the passageway;
   (b) a plurality of links joining the beads together, wherein portions of the links are slidably disposed in corresponding passageways of the beads;
   (c) a clasp assembly that includes a clasp assembly housing, wherein the clasp assembly is configured to removably secure the beads and links in a loop formation;
   (d) a clasp link joining the clasp assembly with one of the beads; and
   (e) an adjustment feature operable to adjust an effective circumference of the loop formation, wherein the adjustment feature includes a clamping feature operable to selectively clamp the clasp link and thereby grip the clasp link, wherein the clamping feature comprises:
      (i) a first clamp plate,
      (ii) a resilient member coupling the first clamp plate to the clasp assembly housing, and
      (iii) a second clamp plate fixedly secured relative to the clasp assembly housing, wherein the clasp link is positioned between the first and second clamp plates.

10. The apparatus of claim 9, wherein the adjustment feature is located in the clasp assembly, wherein the clasp assembly housing contains the clamping feature.

11. An apparatus, the apparatus comprising:
    (a) a plurality of beads, wherein each bead comprises:
       (i) a housing,
       (ii) a passageway extending through the housing, and
       (iii) at least one annular magnet, wherein the at least one annular magnet is coaxially positioned about the passageway;
    (b) a plurality of links joining the beads together, wherein portions of the links are slidably disposed in corresponding passageways of the beads;
    (c) an adjustment feature operable to adjust an effective circumference of a loop formation; and
    (d) a clasp assembly that includes a first clasp member and a second clasp member, wherein the first and second clasp members are configured to removably couple with each other to form the loop formation, wherein the first clasp member comprises:
       (i) a first housing,
       (ii) a first coupling feature, and
       (iii) a first threaded feature, wherein the first threaded feature provides a threaded coupling between the first housing and the first coupling feature.

12. The apparatus of claim 11, wherein the first coupling feature is rotatable relative to the first housing to selectively vary a length defined by the combination of the first housing and the first coupling feature.

13. The apparatus of claim 11, wherein the second clasp member comprises a second coupling feature, wherein the second coupling feature is configured to removably couple with the first coupling feature to thereby selectively secure the first and second clasp members together.

14. The apparatus of claim 13, wherein the second clasp member further comprises:
    (i) a second housing, and
    (ii) a second threaded feature, wherein the second threaded feature provides a threaded coupling between the second housing and the second coupling feature, wherein the second coupling feature is rotatable relative to the second housing to selectively vary a length defined by the combination of the second housing and the second coupling feature.

15. The apparatus of claim 14, wherein the second housing further defines at least one opening, wherein the at least one opening is configured to receive a needle to thereby permit the needle to drive rotation of the second housing relative to the second coupling feature.

16. The apparatus of claim 15, wherein the at least one opening comprises an array of openings that are angularly spaced from one another along an outer peripheral surface of the second housing.

17. The apparatus of claim 11, wherein the first housing further defines at least one opening, wherein the at least one opening is configured to receive a needle to thereby permit the needle to drive rotation of the first housing relative to the first coupling feature.

18. The apparatus of claim 17, wherein the at least one opening comprises an array of openings that are angularly spaced from one another along an outer peripheral surface of the first housing.

19. The apparatus of claim 11, wherein the adjustment feature is located in the clasp assembly.

20. The apparatus of claim 19, wherein the threaded coupling between the first housing and the first coupling feature is operable to adjust the effective circumference of the loop formation.

\* \* \* \* \*